(12) United States Patent
Havens (10) Patent No.: US 7,534,615 B2
(45) Date of Patent: *May 19, 2009

(54) PROCESS FOR DETECTING LEAKS IN SEALED PACKAGES

(75) Inventor: Marvin R. Havens, Greer, SC (US)

(73) Assignee: Cryovac, Inc., Duncan, SC (US)

( * ) Notice: Subject to any disclaimer, the term of this patent is extended or adjusted under 35 U.S.C. 154(b) by 914 days.

This patent is subject to a terminal disclaimer.

(21) Appl. No.: 11/003,175

(22) Filed: Dec. 3, 2004

(65) Prior Publication Data

US 2006/0121613 A1    Jun. 8, 2006

(51) Int. Cl.
*G01N 31/22* (2006.01)

(52) U.S. Cl. .......................... 436/3; 436/127; 436/164; 436/172

(58) Field of Classification Search .............. 436/3, 436/127, 164, 172
See application file for complete search history.

(56) References Cited

U.S. PATENT DOCUMENTS

| | | | |
|---|---|---|---|
| 4,285,697 A | 8/1981 | Neary | |
| 4,526,752 A | 7/1985 | Perlman et al. | |
| 4,772,560 A | 9/1988 | Attar | |
| 4,810,655 A | 3/1989 | Khalil et al. | |
| 4,820,606 A | 4/1989 | Miyasaka et al. | |
| 4,840,919 A | 6/1989 | Attar | |
| 5,043,286 A | 8/1991 | Khalil et al. | |
| 5,096,813 A | 3/1992 | Krumhar et al. | |
| 5,108,932 A | 4/1992 | Wolfbeis | |
| 5,110,530 A | 5/1992 | Havens | |
| 5,114,676 A | 5/1992 | Leiner et al. | |
| 5,211,875 A | 5/1993 | Speer et al. | |
| 5,298,310 A | 3/1994 | Havens | |

(Continued)

FOREIGN PATENT DOCUMENTS

EP    0 524 021 B1    1/1993

(Continued)

OTHER PUBLICATIONS

"A Novel Solid-State Oxygen Sensor", Colvin et al, Johns Hopkins Apl. Tech. Digest, vol. 17, No. 4, 1996, pp. 377-385.

(Continued)

*Primary Examiner*—Lyle A Alexander
(74) *Attorney, Agent, or Firm*—Rupert B. Hurley, Jr.

(57) ABSTRACT

The present invention relates to a process for detecting a leak in a package. The process comprises preparing a package by covering at least a portion of an $O_2$-sensitive product with a multilayer film comprising (i) a leak-indicator layer in which a $O_2$-sensitive indicator is present throughout the leak-indicator layer; and (ii) an $O_2$-barrier layer outward of the leak-indicator layer. A low $O_2$-environment is provided within the package. The leak-indicator layer is then illuminated with light containing a wavelength absorbed by the $O_2$-sensitive indicator, so that the $O_2$-sensitive indicator produces an emission of radiation in an amount inversely proportional to a level of $O_2$ present with the $O_2$-sensitive indicator. Then the multilayer film is scanned while the $O_2$-sensitive indicator is emitting radiation, the scanning being carried out by sensing and comparing the amount of radiation emitted from at least two different regions of the multilayer film.

29 Claims, 2 Drawing Sheets

U.S. PATENT DOCUMENTS

| | | | |
|---|---|---|---|
| 5,310,497 A | 5/1994 | Ve Speer et al. | |
| 5,316,949 A | 5/1994 | Bull et al. | |
| 5,350,622 A | 9/1994 | Speer et al. | |
| 5,358,876 A | 10/1994 | Inoue et al. | |
| 5,407,829 A | 4/1995 | Wolfbeis et al. | |
| 5,439,648 A | 8/1995 | Balderson et al. | |
| 5,458,896 A | 10/1995 | Porter | |
| 5,483,819 A | 1/1996 | Barmore et al. | |
| 5,486,460 A | 1/1996 | Townsend | |
| 5,489,639 A | 2/1996 | Faber et al. | |
| 5,529,833 A | 6/1996 | Speer et al. | |
| 5,583,047 A | 12/1996 | Blinka et al. | |
| 5,617,812 A | 4/1997 | Balderson et al. | |
| 5,686,161 A | 11/1997 | Cullen et al. | |
| 5,744,246 A | 4/1998 | Ching | |
| 5,849,594 A | 12/1998 | Balderson et al. | |
| 5,863,460 A | 1/1999 | Slovacek et al. | |
| 5,904,960 A | 5/1999 | Becraft et al. | |
| 5,911,910 A | 6/1999 | Becraft et al. | |
| 5,912,090 A | 6/1999 | Nagai et al. | |
| 5,993,922 A | 11/1999 | Babrowixz et al. | |
| 6,015,715 A | 1/2000 | Kirschner et al. | |
| 6,023,371 A | 2/2000 | Onitsuka et al. | |
| 6,074,607 A | 6/2000 | Slovacek et al. | |
| 6,139,799 A | 10/2000 | Kimball et al. | |
| 6,190,612 B1 | 2/2001 | Berger et al. | |
| 6,233,907 B1 | 5/2001 | Cook, Jr. et al. | |
| 6,287,481 B1 | 9/2001 | Luthra et al. | |
| 6,297,508 B1 | 10/2001 | Barmore et al. | |
| 6,689,438 B2 * | 2/2004 | Kennedy et al. | 428/36.6 |
| 2003/0008400 A1 | 1/2003 | Putnam et al. | |
| 2003/0082321 A1 * | 5/2003 | Kennedy et al. | 428/35.7 |
| 2003/0108702 A1 | 6/2003 | Tung et al. | |
| 2004/0086749 A1 * | 5/2004 | Kennedy et al. | 428/690 |
| 2004/0131806 A1 * | 7/2004 | Barmore et al. | 428/34.2 |

FOREIGN PATENT DOCUMENTS

| | | |
|---|---|---|
| GB | 2 132 348 | 5/1987 |
| JP | 2003034001 A | 2/2003 |
| JP | 2003307513 | 10/2003 |
| JP | 2003335380 A | 11/2003 |
| WO | 87/00023 A | 1/1987 |
| WO | 98/05703 | 2/1998 |
| WO | 01/63264 A1 | 8/2001 |
| WO | 01/69243 A1 | 9/2001 |
| WO | 02/49923 A2 | 6/2002 |
| WO | 02/051705 A2 | 7/2002 |
| WO | 02/099416 A1 | 12/2002 |

OTHER PUBLICATIONS

"Effects of Polymer Matrices on the Time -Rsolved Luminescence of a Ruthenium Complex Quenched by Oxygen", Draxler et al, J. Pys. Chem., 1995, pp. 3162-3167.

"Photophysics and Photochemistry of Oxygen Sensors Based on Luminescent Transition-Metal Complexes", Carraway et al, Anal. Chem., 1991, pp. 337-342.

"Determination of Oxygen Concentrations by Luminescence Quenching of a Polymer-Immobilized Transition-Metal Complex", Bacon et al, American Chemical Society, 1987, pp. 2780-2785.

"Non-Invasive Method for Determining Oxygen in Food Packaging", Atkinson, Food, Cosmetics and Drug Packaging, Jun. 2000, 2 pages.

Plastics Applications, "PP Woven Container Liners", Plastics Engineering, Aug. 2003, p. 16.

* cited by examiner

PROCESS FOR DETECTING LEAKS IN SEALED PACKAGES

FIELD OF THE INVENTION

The present invention relates to a method of detecting leaks in packages containing an oxygen-sensitive product, i.e., packages having a low oxygen content inside.

BACKGROUND OF THE INVENTION

Oxygen spoils many products. Foods, beverages, pharmaceuticals, medical devices, corrodible metals, analytical chemicals, electronic devices, and many other products may perish or experience diminished shelf life when stored too long in the presence of oxygen. To combat this problem, manufacturers of packaging materials have developed packaging materials and systems to protect these products by providing a package environment, or "headspace", with reduced oxygen levels.

Reduced oxygen levels can be obtained by packaging under vacuum, or by displacing the atmosphere and substituting a modified atmosphere (low in oxygen) around the product. In many cases, the low oxygen level that can be obtained with these packaging systems is still insufficient to provide the desired shelf life.

If a vacuum package or modified atmosphere package develops a leak and allows atmospheric oxygen to enter the package, ultimately the atmospheric oxygen content within the package will increase, with detrimental results on the shelf life of the product. It is known to use a porphyrin as an indicator which can reveal the level of atmospheric oxygen within a package. The porphyrin is excited by illuminating radiation, and the degree to which it thereafter emits radiation (i.e., phosphoresces) is inversely proportional to the level of atmospheric oxygen within the package. However, if the rate at which atmospheric oxygen enters the leaking package is slow, it may require considerable time for the oxygen content inside the package to substantially increase. It would be desirable to be able to quickly determine if a package has a leak immediately after the packaging is complete. It would also be desirable to determine precisely where the leak in the package is.

SUMMARY OF THE INVENTION

The method of the present invention provides a means for determining the presence of a leak, and even the location of the leak, in a vacuum package or a modified atmosphere package, without destruction of the package. The method allows the package to be inspected for leaks repeatedly at different points in the distribution chain, and even by the ultimate consumer. The method allows the package to be inspected for the presence of a leak even before there is any significant increase in the level of atmospheric oxygen inside the package.

The method of the invention involves the use of a multilayer film surrounding at least part of the product, with the film having a oxygen barrier layer to the outside of a second film layer which contains an indicator material, such as a porphyrin. If there is a breach in the film or in a seal of the film to itself or another component of the package, upon illumination of the film to activate the porphyrin, the porphyrin phosphoresces to a degree which is inversely proportional to the oxygen content at that location. A small leak in the package causes the porphyrin in the vicinity of the leak to not phosphoresce or to phosphoresce at a lower level. This lack of phosphorescesce or lowered phosphorescence can be detected by scanning the package for a "dark spot". Scanning can be carried out manually, i.e., with the unaided human eye, or via machine vision. In this manner, immediately after packaging, the package can be inspected for the presence of a leak, and if found to be leaking, can immediately be repackaged. Likewise, after shipping to a distribution and/or retail location, the package can again be tested to determine the presence of a leak which may have been generated during handling or transport. Likewise, the consumer can even check the product again for leaks at retail, to ensure that the package has been effective in maintaining a low oxygen environment to prevent product degradation.

As a first aspect, the present invention pertains to a process for detecting a leak in a package. The process comprises (A) preparing a package by covering at least a portion of an $O_2$-sensitive product with a multilayer film comprising (A)(i) a leak-indicator layer in which a $O_2$-sensitive indicator is present throughout the leak-indicator layer; and (A)(ii) an $O_2$-barrier layer outward of the leak-indicator layer; (B) providing a low $O_2$ environment within the package; (C) illuminating the leak-indicator layer with light containing a wavelength absorbed by the $O_2$-sensitive indicator, so that the $O_2$-sensitive indicator produces an emission of radiation in an amount inversely proportional to a level of $O_2$ present with the $O_2$-sensitive indicator; and (D) scanning the multilayer film while the $O_2$-sensitive indicator is emitting radiation, the scanning being carried out by sensing and comparing the amount of radiation emitted from at least two different regions of the multilayer film. Preferably, at least 25% of product covered by film, more preferably at least 50%, more preferably at least 75%, more preferably 100%.

Preferably, the low $O_2$-environment is provided by carrying out at least one member selected from the group consisting of: (i) scavenging the $O_2$ inside the package by providing the package with an $O_2$-scavenger; (ii) evacuating atmosphere from within the package; and (iii) displacing atmospheric $O_2$ from the package.

Results from the sensing and comparing of the radiation emitted from the at least two different scanned regions correlate with an absence of a leak into the package. Alternatively, results from the sensing and comparing of the radiation emitted from the at least two different scanned regions correlate with a presence of at least one leak into the package. If a leak is detected, preferably, the $O_2$-sensitive product in the package having the at least one leak is removed from the package and repackaged in a new package.

The leak can comprise at least one hole in the multilayer film, or at least one discontinuity in a seal of the film to itself or another component of the package.

Preferably, the package has a seal which is a heat seal.

Preferably, the sensing and the comparing are carried out in a manner capable of determining both the presence and location of at least one leak of atmospheric $O_2$ into the package.

Preferably, the package is made by placing the $O_2$-sensitive product into a bag made by sealing the multilayer film to itself, followed by evacuating atmosphere from within the bag and sealing the inside layer of the bag to itself across an open top of the bag, while the atmosphere is evacuated from the bag. Preferably, the multilayer film has a free shrink at 185° F. of at least 5 percent in both a machine direction and a transverse direction, with the process further comprising heat shrinking the film after the inside layer of the bag is sealed to itself across the open top of the bag. Preferably, the product comprises meat; more preferably, red meat, more preferably, beef, pork, lamb, and/or poultry.

Alternatively, the $O_2$-sensitive product is a non-food product, such as a DVD.

Optionally, the package comprises a formed bottom member and a lidstock sealed to the formed bottom member, with the lidstock comprising the multilayer film. Preferably, the formed bottom member is tray; preferably a polystyrene tray; more preferably a polystyrene foam tray.

In one preferred embodiment, the package comprises a modified atmosphere.

In one preferred embodiment, the $O_2$-sensitive indicator has been printed onto the film.

In a preferred embodiment, the $O_2$-sensitive product scavenges $O_2$ inside the package. Such a product includes beef, pork, poultry, fish.

In a preferred embodiment, the package comprises a tray with an $O_2$-barrier liner, the tray having a flange, with the $O_2$-sensitive product being on the tray, with the multilayer film being over the product and adhered to the tray flange.

In a preferred embodiment, the $O_2$-barrier layer has an oxygen transmission rate of no more than 100 cc/m$^2$/24 hr at 25° C., 0% RH, 1 atm (ASTM D 3985), the $O_2$-barrier layer comprising at least one member selected from the group consisting of polyester, polyamide, ethylene vinyl alcohol copolymer, polyvinyl alcohol homopolymer, polyvinyl chloride, homopolymer and copolymer of polyvinylidene chloride, polyethylene naphthalate, polyacrylonitrile homopolymer and copolymer, liquid crystal polymer, SiO$_x$, carbon, metal, and metal oxide.

In a preferred embodiment the $O_2$-sensitive indicator comprises at least one member selected from the group consisting of metallo derivatives of octaethylporphyrin, tetraphenylporphyrin, tetrabenzoporphyrin, or the chlorins, bacteriochlorins, or isobacteriochlorins thereof.

In a preferred embodiment, the $O_2$-sensitive indicator comprises porphyrin.

In a preferred embodiment the film surrounds the food product.

In a preferred embodiment, atmosphere is evacuated between the food product and the film.

In a preferred embodiment, atmosphere is present between the food product and the multilayer film, the atmosphere containing $O_2$ in an amount of less than 5 weight percent.

In a preferred embodiment, the film further comprises an $O_2$-scavenger which comprises at least one member selected from the group consisting of:

i) oxidizable organic compound and a transition metal catalyst,
ii) ethylenically unsaturated hydrocarbon and a transition metal catalyst,
iii) a reduced form of a quinone, a photoreducible dye, or a carbonyl compound which has absorbence in the UV spectrum,
iv) a polymer having a polymeric backbone, cyclic olefinic pendent group, and linking group linking the olefinic pendent group to the polymeric backbone,
v) a copolymer of ethylene and a strained, cyclic alkylene, and
vi) ethylene/vinyl aralkyl copolymer,
vii) ascorbate,
viii) isoascorbate,
ix) sulfite,
x) ascorbate and a transition metal catalyst, the catalyst comprising a simple metal or salt, or a compound, complex or chelate of the transition metal,
xi) a transition metal complex or chelate of a polycarboxylic acid, salicylic acid, or polyamine,
xii) a tannin, and
xiii) reduced metal.

In a preferred embodiment, the oxygen indicator and the oxygen scavenger are present in the form of a blend. Preferably, the blend is present in a layer of the film.

In a preferred embodiment, the oxygen indicator is encapsulated by an adhesive.

BRIEF DESCRIPTION OF THE DRAWINGS

The accompanying drawings illustrate several embodiments of the invention.

DETAILED DESCRIPTION OF THE INVENTION

As used herein, the phrases "heat-shrinkable film," "heat-shrink film" and the like refers to a film which has been oriented while in the solid state (as opposed to a blown film, which is oriented at, above, or near the melting point of the polymer). The tension on a heat-shrinkable film increases upon the application of heat if the film is restrained from shrinking. As a corollary, the phrase "heat-contracted" refers to a heat-shrinkable film, or a portion thereof, which has been exposed to heat such that the film or portion thereof is in a heat-shrunken state, i.e., reduced in size (unrestrained) or under increased tension (restrained). Preferably, the heat shrinkable film has a total free shrink (i.e., machine direction plus transverse direction), with the free shrink in each direction (measured in accordance with ASTM D 2732) of at least as 5 percent at 185° C., more preferably at least 7 percent, still more preferably, at least 10 percent, still more preferably, at least 15 percent, and, yet still more preferably, at least 20 percent. The total free shrink at 185° F. can be from 10 to 150 percent, more preferably from 20 to 120 percent, more preferably from 40 to 100 percent.

As used herein, the phrases "inner layer" and "internal layer" refer to any layer, of a multilayer film, having both of its principal surfaces directly adhered to another layer of the film.

As used herein, the phrase "outer layer" refers to any film layer of film having less than two of its principal surfaces directly adhered to another layer of the film. The phrase is inclusive of monolayer and multilayer films. In multilayer films, there are two outer layers, each of which has a principal surface adhered to only one other layer of the multilayer film. In monolayer films, there is only one layer, which, of course, is an outer layer in that neither of its two principal surfaces are adhered to another layer of the film.

As used herein, the phrase "inside layer" refers to the outer layer of a multilayer film packaging a product, which is closest to the product, relative to the other layers of the multilayer film.

As used herein, the phrase "outside layer" refers to the outer layer, of a multilayer film packaging a product, which is furthest from the product relative to the other layers of the multilayer film. Likewise, the "outside surface" of a bag is the surface away from the product being packaged within the bag.

As used herein, the term "adhered" is inclusive of films which are directly adhered to one another using a heat seal or other means, as well as films which are adhered to one another using an adhesive which is between the two films.

Although the films used in the process of the present invention can be monolayer films or multilayer films, the patch bag comprises at least two films laminated together. Preferably, the patch bag is comprised of films which together comprise a total of from 2 to 20 layers; more preferably, from 2 to 12 layers; and still more preferably, from 4 to 12 layers. In general, the multilayer film(s) used in the present invention can have any total thickness desired, so long as the film provides the desired properties for the particular packaging operation in which the film is used, e.g. abuse-resistance (especially puncture-resistance), modulus, seal strength, optics, etc.

As used herein, the phrase "low $O_2$-environment" refers to the modified atmosphere environment inside the package in which the atmosphere has either been evacuated, displaced by a different environment, or has reduced $O_2$ content due to the activity of an $O_2$-scavenging agent. Preferably, the low $O_2$-environment has an $O_2$ content of from 0 to 5 percent by volume, more preferably from 0 to 1 percent. If the indicator is a palladium-containing porphyrin, preferably the low $O_2$-environment has an $O_2$ content of from 0 to 5 percent by volume, more preferably from 0 to 1 percent. If the indicator is a platinum-containing porphyrin, preferably the low $O_2$-environment has an $O_2$ content of from 0 to 0.1 percent by volume, more preferably from 0 to 0.05 percent.

Effective shielding to maintain a low $O_2$-environment is a matter of providing the package with an effective $O_2$-barrier layer. Materials which can provide the necessary $O_2$-barrier layer are materials which permit a maximum oxygen transmission rate (OTR) of 100 cc/m²/24 hr at 25° C., 0% RH, 1 atm oxygen (ASTM D 3985). Preferably, the oxygen barrier properties of the barrier layers would permit a maximum OTR of 50 cc/m²/24 hr at 25° C., 0% RH, 1 atm oxygen. More preferably, the oxygen barrier property of the oxygen barrier layer would permit a maximum OTR of 25 cc/m²/24 hr at 25° C., 0% RH, 1 atm oxygen. Most preferably, the oxygen barrier property of the oxygen barrier layer would permit a maximum OTR of 1 cc/m²/24 hr at 25° C., 0% RH, 1 atm oxygen.

All polymeric materials are capable of providing these oxygen permeation rates, provided their cross-sectional thickness is sufficient. A polyethylene, with an oxygen permeability of 2000 cc at a thickness of 1 mil/m²/24 hr at 25° C., 0% RH, 1 atm oxygen, will meet the 100 cc/m²/24 hr at 25° C., 0% RH, 1 atm oxygen barrier requirement described above if the cross-sectional thickness exceeds 20 mils. Materials that are capable of providing the oxygen barrier requirements at very thin cross-sectional thickness include, but are not limited to, polyester, polyamide, ethylene vinyl alcohol copolymer, polyvinyl alcohol homopolymer, polyvinyl chloride, homopolymer and copolymer of polyvinylidene chloride, polyethylene naphthalate, polyacrylonitrile homopolymer and copolymer, and liquid crystal polymer. Additionally, the oxygen barrier properties of polymeric materials can be enhanced by depositing a thin coating of carbon, metal, metal oxide, silica and/or silicon oxide, and $SiO_x$. It is also known that barrier properties of polymeric materials can also be enhanced through melt blending a polymer with glass, clay, and/or a polymer having a relatively low oxygen transmission rate (i.e. a relatively high oxygen barrier). It can also be enhanced through blending polymers, metals, metal halides, etc., with oxygen scavenging materials.

Preferably the multilayer film has a seal layer comprising a sealant material, preferably a heat sealable material. Suitable examples of sealant materials include an olefinic polymer such as ethylene/alpha olefin copolymer, homogeneous ethylene/alpha olefin copolymer, ethylene/vinyl acetate copolymer, ethylene/alkyl acrylate copolymer, ethylene/acrylic acid copolymer, ionomer, propylene homopolymer and copolymer, butylene polymer and copolymer, multi-component ethylene/alpha-olefin interpenetrating network resin, a blend of a propylene homopolymer and a propylene/ethylene copolymer, high density polyethylene, a blend of high density polyethylene and ethylene/vinyl acetate copolymer, a blend of high density polyethylene and low density polyethylene; or a blend of any of these materials; polyamide or copolyamide; or other appropriate polymeric materials. The sealant layer in various films disclosed hereinbelow are positioned as an exterior (surface) layer. This layer will typically be closest to the oxygen sensitive product and serve to provide a means to seal the film to itself or a barrier liner or the like (in the case of a trayed product) during a packaging operation.

Luminescent compounds are compounds that strongly absorb electromagnetic radiation (EMR) at one frequency (the excitation frequency), and emit EMR at the same or another frequency (the emitting frequency). Luminescent compounds appropriate as indicators in the present invention will luminesce only in the absence of $O_2$. More precisely, the indicators will luminesce upon exposure to their excitation frequency only when $O_2$ concentration falls below a threshold level. As long as the concentration of $O_2$ to which the indicators are exposed exceeds threshold levels, the oxygen will prevent, or "quench" luminescence.

A porphyrin is a preferred indicator for use in the process of the present invention. Porphyrins include physiologically active nitrogenous compounds occurring widely in nature (e.g., chlorophyll), as well as synthetic nitrogenous compounds which can be prepared by passing an electric current through a mixture of ammonia, methane, and water vapor. The structure of a porphyrin includes four pyrrole rings, together with four nitrogen atoms and two replaceable hydrogens, for which various metal atoms can be readily substitute. In the preferred porphyrins for use in the process of the present invention, platinum or palladium replace the replaceable hydrogens in the center of the compound. The structure of two preferred porphyrins are set forth immediately below.

-continued
OCTAETHYLPORPHYRIN

Me = Pt, Pd

Porphyrin compounds phosphoresce in the absence of oxygen (i.e., $O_2$) when illuminated by certain wavelengths of light, particularly longer wavelength ultraviolet light. The phosphorescence is quenched by $O_2$, limiting the relative brightness or lifetime of the phosphorescent light produced. The relationship of this light intensity or duration is inversely proportional to the amount of $O_2$ present. Platinum, palladium and other metal porphyrins perform similarly but a different relative levels of oxygen, and with different senstivities to a change in oxygen concentration.

By proper choice of pendant groups, porphyrins can be rendered more or less soluble or dispersable in different resins and/or inks. A suitable porphyrin can be dissolved or dispersed into a resin that is then incorporated into a film layer, or dissolved or dispersed into an ink that this then printed onto the surface of an $O_2$-barrier film, with the $O_2$-barrier film then being used to make a package containing a low $O_2$ level inside the package.

The term "luminescent" as used herein, encompasses phosphorescence, fluorescence, or any electromagnetic emission that can serve the indicator function. When the emission frequency is in the visible spectrum, the indicator may be read by either machine or the human eye. When the emission frequency is not visible, luminescence may be detected by machine.

Luminescent compounds suitable for use in this invention include any known or after-discovered compounds having the functionality just described. Additionally, suitable luminescent compounds and compositions comprising them preferably have one or more of the following characteristics as well:

a) Their response to changes in oxygen concentration are predictable, linear, and fully reversible. Linearity is desirable for calibration and quantitative monitoring purposes. Reversibility allows the oxygen concentration to be monitored at any stage of the packaging and storage process;

b) They are sensitive to oxygen concentrations within target ranges. Ranges can include between 0% and 5% oxygen, such as between 0% and 1%, or between 0 to 1000 ppm. Combinations of indicators having different ranges and sensitivities may be used to extend such ranges if desirable;

c) They respond quickly to changes in oxygen concentration in the conditions in which they will be used. A typical response time of a luminescent compound to a change in oxygen concentration is within 1 minute or less of the atmosphere change over a temperature range of between 0° C. and 25° C.;

d) They exhibit luminescence over a range of frequencies easily monitored. For use with an inexpensive interrogative device, the indicator(s) should have suitable excitation and emission frequencies, preferably visible;

e) They are selectively responsive to oxygen concentration changes and insensitive to other gases that may permeate the dye containing packaging material, such as carbon dioxide;

f) They are stable under conditions of use and storage. Photostability is desirable but not required. temperature stability, and stability to changes in humidity, are desirable and preferred;

g) They are clear or color-compatible with the packaging in which they are used. Color-compatibility is important for example where the indicator may form all or part of a printed image. In embodiments where a discrete patch is used, clarity or color compatibility is usually not as important;

h) They exhibit good coating and/or printability properties, and/or are amenable to extrusion; and i) The indicator is useful in relatively low concentrations in order to minimize the cost of the overall packaging material.

Preferred luminescent compounds for use in this invention include fluorescent or phosphorescent dyes that exhibit oxygen quenched luminescence. Phosphorescent dyes are preferable to fluorescent dyes for oxygen sensing as the former are characterized by well separated excitation and emission frequencies. These frequencies are commonly in the visible region of the spectrum and have long excited-state lifetimes. Phosphorescent dyes also have improved sensitivity to low levels of oxygen to facilitate monitoring.

Compounds suitable as indicators in the context of this invention are known in the art. For example, Khalil et al., U.S. Pat. Nos. 4,810,655 and 5,043,286, both incorporated by reference, disclose suitable compounds and methods for their manufacture. Such compounds include metallo derivatives of octaethylporphyrin, tetraphenylporphyrin, tetrabenzoporphyrin, or the chlorins, bacteriochlorins, or isobacteriochlorins and their partially or fully fluorinated analogs. Other suitable compounds include palladium coproporphyrin (Pd-CPP), platinum and palladium octaethylporphyrin (PtOEP, PdOEP), platinum and palladium tetraphenylporphyrin (Pt-TPP, PdTPP), camphorquinone (CQ), and xanthene type dyes such as erythrosin B (EB). Other suitable compounds include ruthenium, osmium and iridium complexes with ligands such as 2,2'-bipyridine, 1,10-phenanthroline, 4,7-diphenyl-1,10-phenanthroline and the like. Suitable examples of these include, tris(4,7,-diphenyl-1,10-phenanthroline)ruthenium (II) perchlorate, tris(2,2'-bipyridine)ruthenium(II) perchlorate, and tris(1,10-phenarithroline)ruthenium(II) perchlorate. While the perchlorate salts are particularly useful, other counterions that do not interfere with the luminescence may be used.

Alternative Oxygen Sensitive Fluorescing Materials include the following:

Rhenium Complexes—Re(I)

Where:

L=α-diimine

R=aliphatic group (*Analytical Chemistry* 1995, 67, 1377-1380, hereby incorporated by reference thereto)

Erythosine B (Analyst, February 1995, V120, p 457, hereby incorporated by reference thereto)

Other Porphyrin Metals

Zn
Lu (Lutetium)
Sn
Pb
Pt
Pd
Hf
(*J chem. Soc* perkin trans, 2 1995, p 103, hereby incorporated by reference)

Ruthenium Complex

Ru(II)
(*J phys chem.* 1995, 99, 3162-3167, hereby incorporated by reference)

Ruthenium Complex

Tris(2,2'-pipyridyl)Ru(II) dichloride, also known as RuBIPPY

Sensors and Actuators B 29, (1995) 251-257, hereby incorporated by reference

Compositions comprising one or more indicator compounds will preferably be dissolved in a polymeric carrier or solvent matrix (system). There are two reasons for this. One reason is that solution achieves the maximum dispersion and therefore utilization of the indicator compound for maximum efficiency. The other is that agglomeration of the indicator compounds must be avoided because of an adverse interaction between two indicator molecules that results in self quenching and reduced efficiency. It is well known that the polymer matrix can influence the luminescence decay of the indicator (see J. Phys. Chem., 1995, 99, 3162-3167).

The indicator composition can be chosen for maximum solubility in the polymer or solvent system. One can change the solubility of a ligand indicator in a polymer or solvent matrix by varying the substituent group(s) on the ligand. For example, one can substitute non-fluorinated porphyrins for partially or fully fluorinated porphyrins, or tetraphenyl porphyrins for octaethyl porphyrins, or the like, to select the porphyrin having the solubility in a polymer or solvent matrix desired. Where the complexes involve counterions, the selection of the counterion can influence the solubility of the compound in the polymer matrix.

Those skilled in the art will understand that only a very minor amount of indicator is needed to achieve luminescence sufficient for good detection. Indicator compounds are preferably used in relatively low concentrations in order to minimize cost of the overall packaging material. Suitable concentrations of indicator compounds can be from a few micrograms per square inch (area) to a few milligrams per square inch (area).

The various embodiments of the present invention are based in part on the choices of polymer or solvent system and necessary concentrations for the indicator compound. If an indicator is sufficiently heat stable, it can be effectively dissolved in a polymer and extruded. One can achieve a suitable area concentration to observe luminescence by adjusting the indicator concentration and the polymer thickness. Furthermore, this indicator and polymer system can be extruded in several ways to be incorporated into a suitable solid. For example, the indicator can be dispersed in a monolayer film or in one or more layers of a multilayer film that also includes a barrier layer or coating. The monolayer or multilayer film can be cut to form an appliqué and attached to a suitable backing material.

If the indicator compound is more compatible with specific solvents, it can be incorporated into a solvent and/or ink system and effectively printed onto a suitable film or substrate. As part of a suitable ink system, the indicator compound could be trap printed along with the graphics that comprise the oxygen scavenging film.

In order to be effective in revealing the presence of a leak in the package, the porphyrin should be located inside the package relative to the position of the $O_2$-barrier layer in the film. In this manner, upon illumination (i.e., upon excitation), the porphyrin phosphoresces at a level which is inversely proportional to the $O_2$ in its immediate vicinity. A package having a low internal $O_2$ environment allows the porphyrin to phosphoresce strongly, with the $O_2$ present around any small leak quenching (or dimming) the phosphorescence of the porphyrin in the immediate vicinity of the leak, thereby revealing the leak by contrasting the absence of phosphorescence around the leak with the higher level of phosphorescence at a distance from the leak. Relative phosphorescence is readily discerned under ultraviolet illumination (e.g., blacklight) in a darkened room. The relative color/brightness differences can be even more readily discerned with the use of blue absorbing lenses which further enhance the visual color contrast.

By scanning for this difference in phosphorescence level, the small leaks can be detected, as the leak appears as a dark spot surrounded by a bright area. If the leak is a large leak which allows so much $O_2$ to enter the package that the $O_2$ level within the package is high enough to quench the phosphorescence activity of the porphyrin throughout all or a substantial portion of the package, the scanning will reveal this absence of phosphorescence and thereby confirm the presence of one or more substantial leaks in the package.

Using the method of the invention, the presence of even a small leak in a package can be detected almost as soon as the leak is present. In this manner, packages can be tested for the presence of leaks as soon as the package is made, while there is still an opportunity to remove $O_2$-sensitive product from leaking package, repackage it and the retest it for the presence of one or more leaks. In this manner, the number of leaking packages being shipped from the packer can be reduced or eliminated.

Scanning packages for the presence of one or more leaks can be carried out manually (i.e., with the unaided human eye), or using an automated imaging system (e.g., machine vision), such as are available from Cognex or DVT. Using either system, packages determined to be leak-free can be passed on to distribution, with packages determined to be leaking being diverted for repackaging. An automated imaging system can be designed to be more sensitive than the human eye at detecting a leak, and can also be designed to discern the edges and surfaces of the package.

Machine Vision utilizes a machine (e.g., a computer) in combination with some form of image generator (e.g., a camera) to determine whether particular, predetermined features are present in an object being assessed. Depending upon the image generator sensing the presence or absence of one or more predetermined features, the machine communicates with an action device so that some action or non-action is taken. Thus, action is either taken or not taken, depending upon the content of the image sent from the camera to the computer. The image capture and processing can detect and take into account spatial relationships, such as edges, colors, etc. Machine vision is well known, as is apparent from educational courses dedicated to the subject. See the textbook

*Image Processing, Analysis and Machine Vision* by Sonka, et. al. Brooks/Cole Publishing, Pacific Grove, Calif. 1999, which is incorporated in its entirety by reference thereto.

In the present invention, the oxygen-quenched porphyrin-containing layer within the package is illuminated with a wavelength of light that excites the porphyrin to phosphoresce. The illumination is carried out using ultraviolet wavelengths of a UV-A black-light, i.e., around 360 to 400 nm. The presence of atmospheric oxygen in the vicinity of the porphyrin quenches this phosphorescence. However, in the absence of oxygen, the phosphorescence is persistent and therefore, visible. The phosphorescence from the porphyrin is of visible light in the wavelength of around 660 nm, a carmine red color.

Scanning can be carried out manually using the unaided eye. However, if machine vision scanning is desired, it can be carried out with a suitable camera device coupled with a suitable computer. The image picked up by the camera has three basic colors: a black background color, a combination of violet (from the UV-A bulb) plus a small spill over of green light (also from the UV-A bulb) with the red color of the excited, low oxygen porphyrin. These colors are captured in each pixel's information. Depending on the camera chosen and its distance from the product, each pixel would have dimensions of from a few mils to one eighth of an inch, relative to the package surface.

The computer (or unaided eye) can readily process the image for color and intensity. Colors, such as carmine red, are readily identified. A visual edge, such as the edge of the package, is readily determined by comparison of pixels on one side of a boundary (e.g., the black background) and not on the other side (e.g., the violet and green of the UV-A bulb and/or the red absence of oxygen color) on the package surface. Within the visual boundaries of the package, the computer looks at and compares areas by their red (oxygen absent color) or UV-A blacklight bulb colors. The computer can be programmed to discriminate and ignore individual random pixels of black on a red field as "noise", but can take appropriate action if there are any extended areas of black within the red field of the package's visual boundary. Extended areas without the red color indicate the presence of oxygen, i.e., the presence of a leak. The computer can be programmed to take action upon identification of one or more black spots in a field of red, to cause the package to be further inspected and/or diverted for re-packaging. In this way, packages are inspected for leaks (and repackaged if a leak is detected), so that no leaking packages are sent out from the packaging site.

Scanning can be carried out on part or all of the package. If machine vision scanning is used, one means of scanning the entire package is with several cameras which together provide one or more images covering the entire surface of the package. Alternatively, a single camera can be used in combination with some means for scanning the entire package, such as rotating the package while in the view of the camera, or rotating the camera around the package, to obtain one or more images which taken alone or together cover all sides of the package.

Commercial machine vision hardware and supporting software suitable for adaptation to this invention is available from various sources, including Cognex Corporation, located at One Vision Drive, Natick, Mass. 01760-2059 Natick, Mass. (contact via web at www.cognex.com, or (508) 650-3000). Another source for machine vision equipment is DVT Corporation, at DVT US Headquarters, 1855 Satellite Blvd, Suite 100, Duluth, Ga. 30097-4061(at www.dvtsensors.com or 770-814-7920). In addition, there are a large number of companies that can custom assemble such systems from available hardware and software. That portion of the *Thomas Register* 2003 has fourteen pages of company listings under the general title of "machine vision."

Automated scanning can be assisted by including anywhere in the film an appropriate amount of a second ultraviolet fluorescing compound which is non-$O_2$-sensing, allowing the package to "glow" against an otherwise black background. Of course, this second ultraviolet fluorescing compound should fluoresce at a frequency which differs from the frequency of the phosphorescence of the leak indicator compound. Compounds which can be used as the second ultraviolet fluorescing compound include compounds classified as benzoxazoles. A preferred benzoxazole is 2,5-thiophenediyl-bis(5-tert-butyl-1,3-benzoxazole). For example, this compound absorbs the shorter wavelength UV illumination that excites the oxygen sensitive fluorescing compound but emits a higher frequency light in the green-yellow range. A machine vision system can then use the differences between the two wavelength emissions to identify the package edge, that is the boundary between "dark" and "yellow-green" and then look for the relative intensity of the reddish emission of the oxygen sensitive fluorescing compound. This further assists in locating a leak along an edge of the package, which would otherwise appear identical to the "dark background" seen by the vision system.

In the scanning of the multilayer film, an optical or digital filter can be used to enhance sensitivity to the excited emission wavelength (i.e., the wavelength of the phosphorescence emitted by the indicator compound). The excited emission wavelength can then be scanned by a rastering system, such as a television camera, or captured as an optical image focused on a suitable array detector, such as a CCD (charge coupled device). The captured image can then be analyzed for the relative excited emission intensity. For the appropriate wavelength, a dark region surrounded by a bright region would indicate a leak because the emission would be oxygen quenched in that immediate area, resulting in a dark area.

To insure full coverage of the finished package, it will be necessary to observe all sides. In one embodiment, several fixed light sources and fixed detector systems are used to fully view all sides of the finished package. Alternatively, a single light source and detector can be moved around the product for full coverage of all sides. Alternatively, the finished package can be moved around within the view of a single fixed light source and fixed detector system and thereby achieve full view of all sides.

In one embodiment, the indicator is present in the film layer in an amount of from about 0.001 milligram per square meter to 20 milligram per square meter; preferably 0.01 to 2 $mg/m^2$; more preferably 0.1 to 1 $mg/m^2$; more preferably 0.2 to 0.5 $mg/m^2$. If scanning for leaks is to be carried out by the unaided human eye more indicator may be required than if machine vision is being used, as machine vision equipment can be more made more sensitive to detecting color differences than the human eye is.

The indicator can either be blended in with a film layer, or printed on the inside surface of the film or between two film layers of a laminated multilayer film. If printed on, the is present in an ink composition. Although it is preferable to have the indicator present throughout the package, it is not necessary to do so. For example, it may be preferable to provide the indicator only in the areas susceptible to having a leak, such as in seal areas, areas subjected to abuse, etc. Although an oxygen scavenger can be used in the film, as set forth above, in some instances it is preferable that the film contains no oxygen scavenger, indeed, that the package contains no oxygen scavenger.

Many "fresh" products, such as meat, are capable of reactions with atmospheric $O_2$. That is, such products are effectively $O_2$-scavengers. Such products which scavenge $O_2$ from inside the package can reduce the $O_2$ concentration inside the package to a level where the porphyrin can phosphoresce upon being illuminated.

The film used in the process of the present invention can further comprise an $O_2$-scavenger in one or more layers inward of the $O_2$-barrier layer of the film. The scavenger can operate both to retain a low $O_2$-level inside the package, and to ensure that the indicator layer is not prevented from phosphorescing due to the presence of enough $O_2$ within the package to quench the indicator. Moreover, it has been found that the presence of a film layer containing an $O_2$-scavenger does not impair the ability to carry out the process of the present invention, because the rate of $O_2$ scavenging is considerably lower than the ability of $O_2$ at a leak location to quench the indicator at that location. The scavenger can even be present in the layer which contains the indicator.

Details regarding the structure and use of the indicator, especially in conjunction with the use of the indicator in packaging films, as well as detection of phosphorescence from the indicator in packaging films, particularly in conjuction with the presence of an oxygen scavenger in the packaging film, are set forth in copending U.S. Ser. No. 09/875,515, entitled "Oxygen Detection System for a Solid Article", filed Jun. 6, 2001, published May 1, 2003, as US 2003/0082321 A1, which is hereby incorporated, in its entirety, by reference thereto.

In these cases, packagers find it advantageous to ensure against the presence of atmospheric oxygen by including in the package oxygen scavenger within a low oxygen modified atmosphere package (MAP) or a vacuum package (VP). Packaging materials that include oxygen scavengers have grown increasingly sophisticated in recent years. For example, Speer et al. have developed clear, multi-layered packaging films that incorporate an oxygen scavenging composition within its layers. See U.S. Pat. Nos. 5,529,833, 5,350,622, and 5,310,497.

Figure 1:
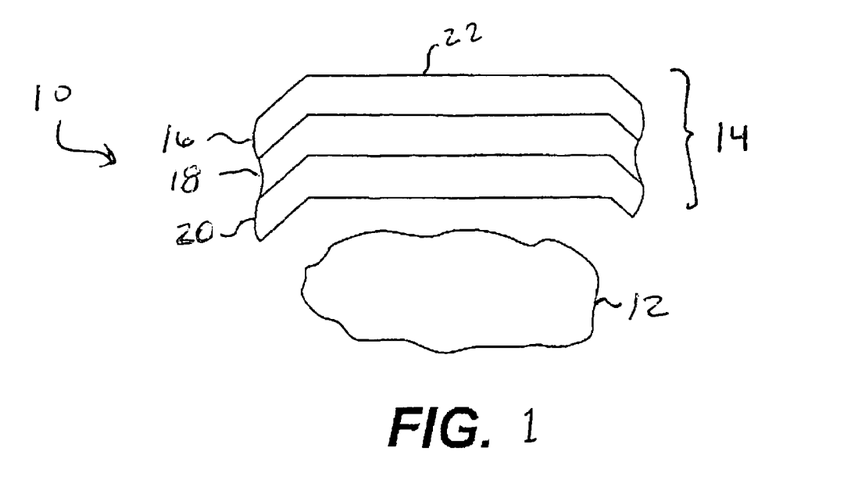
FIG. 1 is a schematic of a bag-type packaged product for use in the process of the invention, the package containing an $O_2$-sensitive product surrounded by a multilayer film a fragment of which is illustrated in cross-sectional view.

FIG. 1 is a fragmentary schematic representing a packaged product for use in the process of the present invention. Packaged product 10 has $O_2$-sensitive product 12 surrounded by multilayer film 14, which comprises $O_2$-barrier layer 16, indicator layer 18, and seal layer 20. Although multilayer film 14 entirely surrounds $O_2$-sensitive product 12, FIG. 1 shows only a fragmentary view of film 14. In FIG. 1, it should be noted that indicator layer 18 is located to the "inside" of $O_2$-barrier layer 16, i.e., indicator layer 18 is positioned further inside outer surface 22 of packaged product 10 relative to $O_2$-barrier layer 18. This is important because $O_2$-barrier layer 18 prevents atmospheric $O_2$ from quenching the phosphorescence of indicator layer 18.

Figure 2:
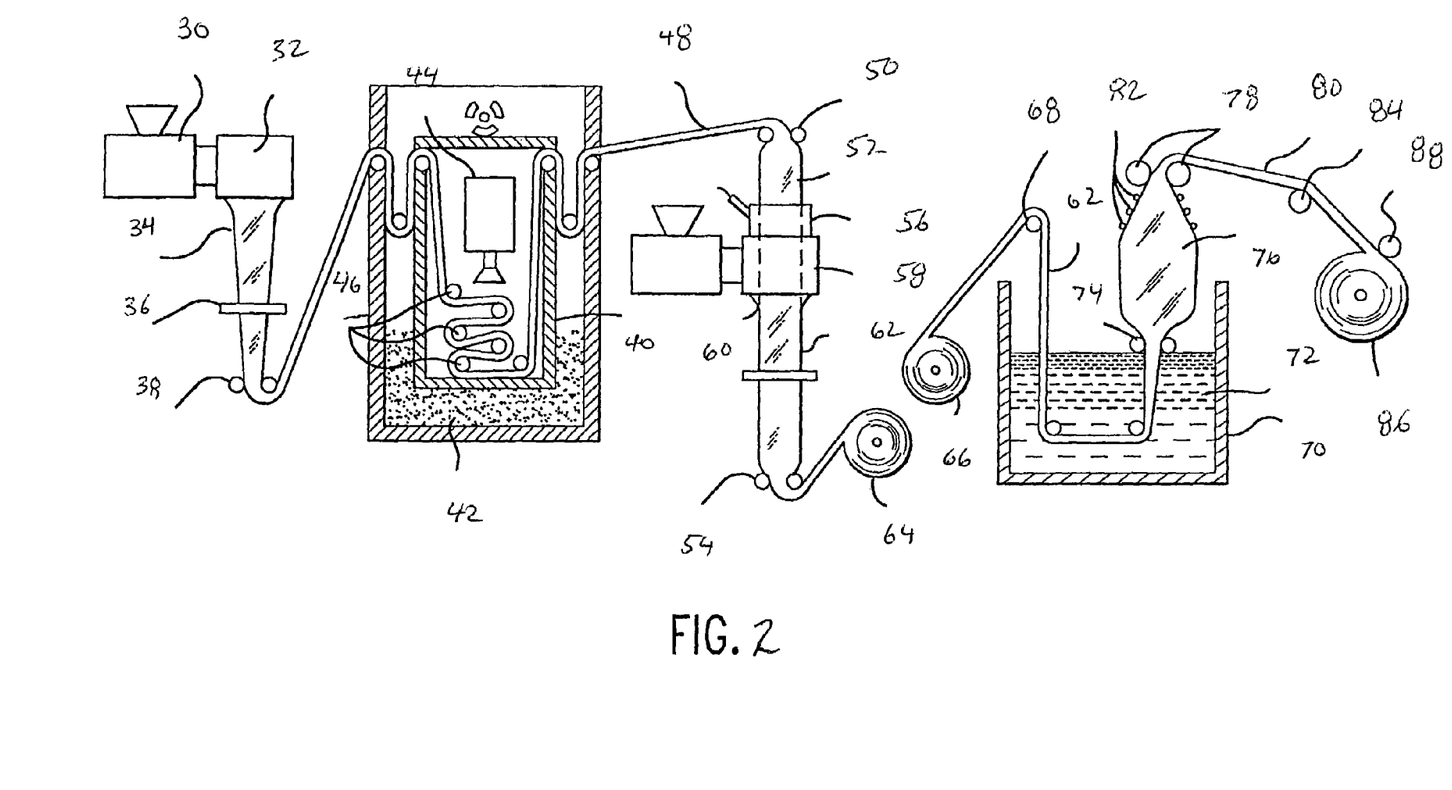
FIG. 2 is a schematic of a process for making a film for use in the process of the present invention.

FIG. 2 illustrates a schematic of a preferred process for producing the multilayer films described in Tables I-VIII, below. In the process illustrated in FIG. 2, solid polymer beads (not illustrated) are fed to a plurality of extruders 30 (for simplicity, only one extruder is illustrated). Inside extruders 30, the polymer beads are forwarded, melted, and degassed, following which the resulting bubble-free melt is forwarded into die head 32, and extruded through an annular die, resulting in tubing 34 which is 10 to 30 mils thick, more preferably 15 to 25 mils thick.

After cooling or quenching by water spray from cooling ring 36, tubing 34 is collapsed by pinch rolls 38, and is thereafter fed through irradiation vault 40 surrounded by shielding 42, where tubing 34 is irradiated with high energy electrons (i.e., ionizing radiation) from iron core transformer accelerator 44. Tubing 34 is guided through irradiation vault 40 on rolls 146. Preferably, tubing 34 is irradiated to a level of about 4.5 MR.

After irradiation, irradiated tubing 48 is directed through nip rolls 50, following which tubing 48 is slightly inflated, resulting in trapped bubble 52. However, at trapped bubble 52, the tubing is not significantly drawn longitudinally, as the surface speed of nip rolls 54 are about the same speed as nip rolls 50. Furthermore, irradiated tubing 48 is inflated only enough to provide a substantially circular tubing without significant transverse orientation, i.e., without stretching.

Slightly inflated, irradiated tubing 48 is passed through vacuum chamber 56, and thereafter forwarded through coating die 58. Second tubular film 170 is melt extruded from coating die 58 and coated onto slightly inflated, irradiated tube 48, to form two-ply tubular film 62. Second tubular film 60 preferably comprises an $O_2$-barrier layer, which does not pass through the ionizing radiation. Further details of the above-described coating step are generally as set forth in U.S. Pat. No. 4,278,738, to BRAX et. al., which is hereby incorporated by reference thereto, in its entirety.

After irradiation and coating, two-ply tubing film 62 is wound up onto windup roll 64. Thereafter, windup roll 64 is removed and installed as unwind roll 66, on a second stage in the process of making the tubing film as ultimately desired. Two-ply tubular film 62, from unwind roll 66, is unwound and passed over guide roll 68, after which two-ply tubular film 62 passes into hot water bath tank 70 containing hot water 72. The now collapsed, irradiated, coated tubular film 62 is submersed n hot water 72 (having a temperature of about 210° F.) for a retention time of at least about 5 seconds, i.e., for a time period in order to bring the film up to the desired temperature for biaxial orientation. Thereafter, irradiated tubular film 62 is directed through nip rolls 74, and bubble 76 is blown, thereby transversely stretching tubular film 62. Furthermore, while being blown, i.e., transversely stretched, nip rolls 78 draw tubular film 62 in the longitudinal direction, as nip rolls 78 have a surface speed higher than the surface speed of nip rolls 74. As a result of the transverse stretching and longitudinal drawing, irradiated, coated biaxially-oriented blown tubing film 80 is produced, this blown tubing preferably having been both stretched in a ratio of from about 1:1.5-1:6, and drawn in a ratio of from about 1:1.5-1:6. More preferably, the stretching and drawing are each performed a ratio of from about 1:2-1:4. The result is a biaxial orientation of from about 1:2.25-1:36, more preferably, 1:4-1:16. While bubble 76 is maintained between pinch rolls 74 and 78, blown tubing film 80 is collapsed by rolls 82, and thereafter conveyed through nip rolls 78 and across guide roll 84, and then rolled onto wind-up roll 86. Idler roll 88 assures a good wind-up.

The polymer components used to fabricate multilayer films for use in making the bags, lids, etc., for use in the present invention may also contain appropriate amounts of other additives normally included in such compositions. These include antiblocking agents (such as talc), slip agents (such as fatty acid amides), fillers, pigments and dyes, radiation stabilizers (including antioxidants), fluorescence additives (including a material which fluoresces under ultraviolet radiation), antistatic agents, elastomers, viscosity-modifying substances (such as fluoropolymer processing aids) and the like additives known to those of skill in the art of packaging films.

The multilayer films for use in the process of the present invention are preferably irradiated to induce crosslinking, as well as corona treated to roughen the surface of the films which are to be adhered to one another. As can be seen in the process of FIG. 2, the film is made by extruding a substrate, which is quenched and irradiated before additional layers are extrusion coated thereon. Since indicators (including porphyrin indicators) can be permanently inactivated if subjected to irradiation at a level of 70 kGy, i.e., a typical level of irradiation of the substrate, the layer containing the porphyrin is preferably included only in one or more of the layers of the extrusion coating, as these layers are not subjected to irradiation. Preferably, the porphyrin is included a tie layer inside of the $O_2$-barrier layer.

In the irradiation process, the film is subjected to an energetic radiation treatment, such as corona discharge, plasma, flame, ultraviolet, X-ray, gamma ray, beta ray, and high energy electron treatment, which induce cross-linking between molecules of the irradiated material. The irradiation of polymeric films is disclosed in U.S. Pat. No. 4,064,296, to BORNSTEIN, et. al., which is hereby incorporated in its entirety, by reference thereto. BORNSTEIN, et. al. Discloses the use of ionizing radiation for crosslinking the polymer present in the film.

Radiation dosages are referred to herein in terms of the radiation unit "RAD", with one million RADS, also known as a megarad, being designated as "MR", or, in terms of the radiation unit kiloGray (kGy), with 10 kiloGray representing 1 MR, as is known to those of skill in the art. A suitable radiation dosage of high energy electrons is in the range of up to about 16 to 166 kGy, more preferably about 40 to 90 kGy, and still more preferably, 55 to 75 kGy. Preferably, irradiation is carried out by an electron accelerator and the dosage level is determined by standard dosimetry processes. Other accelerators such as a van der Graaf or resonating transformer may be used. The radiation is not limited to electrons from an accelerator since any ionizing radiation may be used.

As used herein, the phrases "corona treatment" and "corona discharge treatment" refer to subjecting the surfaces of thermoplastic materials, such as polyolefins, to corona discharge, i.e., the ionization of a gas such as air in close proximity to a film surface, the ionization initiated by a high voltage passed through a nearby electrode, and causing oxidation and other changes to the film surface, such as surface roughness.

Corona treatment of polymeric materials is disclosed in U.S. Pat. No. 4,120,716, to BONET, issued Oct. 17, 1978, herein incorporated in its entirety by reference thereto, discloses improved adherence characteristics of the surface of polyethylene by corona treatment, to oxidize the polyethylene surface. U.S. Pat. No. 4,879,430, to HOFFMAN, also hereby incorporated in its entirety by reference thereto, discloses the use of corona discharge for the treatment of plastic webs for use in meat cook-in packaging, with the corona treatment of the inside surface of the web to increase the adhesion of the meat to the adhesion of the meat to the proteinaceous material. Although corona treatment is a preferred treatment of the multilayer films used to make the patch bag of the present invention, plasma treatment of the film may also be used.

A multilayer film is preferably converted to the bags for use in the process of the present invention by heat sealing a tubular film (i.e., backseamed or seamless) to make a lay-flat bag which is an end-seal bag or a side-seal bag. Similarly, two pieces of flat film can be sealed to one another to make a U-sealed pouch, or a flat film can be folded over and sealed to itself to make a side-seal bag or an L-seal bag. One or more patches can be provided on the bag. End-seal, side-seal, and L-seal bags, and patches thereon, are disclosed in U.S. Pat. No. 6,383,537 B1, entitled "Patch Bag Having Overhanging, Bonded Patches", which is hereby incorporated, in its entirety, by reference thereto.

Figure 3:
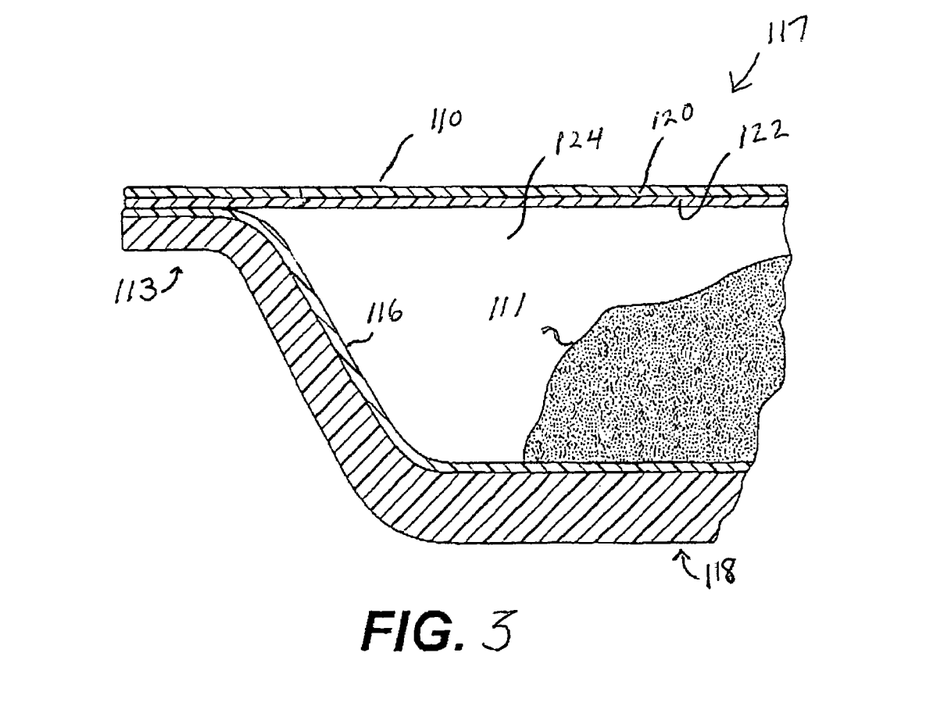
FIG. 3 is a cross-sectional view of a tray-type packaged product for use in the process of the invention, the package containing an $O_2$-sensitive product over which is a multilayer film lidding film.

FIG. 3 illustrates a cross-sectional view of a portion of a packaged product 117 including tray 118 having $O_2$-barrier liner film 116 adhered to an inside surface thereof, $O_2$-sensitive product 111 (such as ground beef) disposed in tray 118, and multilayer lidding film 110 adhered or sealed to barrier film 116 at tray flange 113. Multilayer lidding film 110 has outer $O_2$-barrier layer 120 and inner seal and indicator layer 122. Headspace 124 contains a low $O_2$ modified atmosphere. Barrier liner film 116 can be monolayer or multilayer in composition, and includes an oxygen barrier layer of the type disclosed herein. Suitable olefinic sealants, comprising olefinic materials of the type disclosed herein, can form separate layers in the barrier liner. A typical five-layer construction for barrier liner 116 is:

olefin polymer or copolymer/tie/EVOH/tie/olefin polymer or copolymer

Table I, below, provides a preferred multilayer film structure for use in the present invention, including the composition, thickness, and general function of each of the film layers. This film, extruded from an annular die and thereafter extrusion coated, was in the form of a seamless tubing and had a total thickness of approximately 2.4 mils, and exhibited a total free shrink at 185° F. of 20% in the machine direction and 33% in the transverse direction.

TABLE I

| Layer Function | Layer Chemical Identity | Layer Thickness (mils) |
|---|---|---|
| Outside and abuse layer | 90% EVA #1 10% HDPE #1 | 0.58 |
| $O_2$-Barrier layer | 96% VDC/MA #1; 2% epoxidized soybean oil; and 2% bu-A/MA/bu-MA terpolymer | 0.19 |
| Puncture-resistant & Indicator Layer | 85% LLDPE #1 &15% EBA #1 | 1.15 |
| Sealant and inside layer | 80% SSPE#1 20% LLDPE #2 | 0.48 |

In Table I, LLDPE #1 was DOWLEX® 2045 linear low density polyethylene, obtained from the Dow Chemical Company of Midland, Mich. LLDPE #2 was ESCORENE® LL3003.32 linear low density polyethylene, obtained from Exxon Chemical Company of Baytown, Tex. SSPE#1 was AFFINITY® Pl1280 metallocene-catalyzed ethylene/octene copolymer, having a density of 0.900 g/cc and a melt index of 6 g/10 min, obtained from The Dow Chemical Company, of Midland, Mich. HDPE #1 was Fortiflex® T60-500-119 high density polyethylene, obtained from Solvay Polymers, of Deer Park, Tex. EVA No. 1 was ESCORENE® LD318.92 ethylene/vinyl acetate copolymer having a melt index of 2.0, a density of 0.930 g/cc, and a vinyl acetate mer content of 9 percent, this resin being obtained from the Exxon Chemical Company. EBA No. 1 was SP 1802 ethylene/butyl acrylate copolymer containing 18% butyl acrylate, obtained from Chevron Chemical Company, of Houston, Tex.

Table II, below, provides another preferred multilayer film structure for use in the present invention, the film having a total thickness of 3 mils and a free shrink at 185° F. of 28 percent in the machine direction and 36 percent in the transverse direction.

TABLE II

| Layer Function | Layer Chemical Identity | Layer Thickness (mils) |
|---|---|---|
| Outside and abuse layer | 80% SSPE2 20% LLDPE3 | 0.21 |
| Core Layer | 100% LLDPE2 | 0.32 |
| Tie Layer | 100% EMA | 0.11 |
| $O_2$-Barrier layer | 96% VDC/MA #1; 2% epoxidized soybean oil; and 2% bu-A/MA/bu-MA terpolymer | 0.21 |
| Tie Layer & Indicator layer | 100% EVA1 | 0.11 |
| Substrate Core Layer | 60% LLDPE2 40% LLDPE3 | 1.5 |
| Seal Layer | 60% SSPE1 40% LLDPE 1 | 0.56 |

Table III, below, provides another preferred multilayer film structure for use in the present invention, the film having a total thickness of about 2.2 mils and a free shrink at 185° F. of about 31% in the machine direction and about 44% in the transverse direction.

TABLE III

| Layer Function | Layer Chemical Identity | Layer Thickness (mils) |
|---|---|---|
| Outside and abuse layer | 85% SSPE2 15% LLDPE3 | 0.19 |
| Core Layer | 100% LLDPE2 | 0.29 |
| Tie Layer | 100% EMA | 0.1 |
| $O_2$-Barrier layer | 96% VDC/MA; 2% epoxidized soybean oil; and 2% bu-A/MA/bu-MA terpolymer | 0.19 |
| Tie Layer & Indicator Layer | 100% EVA1 | 0.1 |
| Substrate Core Layer | 80% LLDPE2 20% LLDPE3 | 0.86 |
| Seal Layer | 80% SSPE1 20% LLDPE1 | 0.48 |

Table IV, below, provides another preferred multilayer film structure for use in the present invention, the film having a total thickness of 2.3 mils and a free shrink at 185° F. of 25 in the machine direction and 41 in the transverse direction.

TABLE IV

| Layer Function | Layer Chemical Identity | Layer Thickness (mils) |
|---|---|---|
| Outside and abuse layer | 100% EVA4 | 0.6 |
| $O_2$-Barrier layer | 96% VDC/MA #1; 2% epoxidized soybean oil; and 2% bu-A/MA/bu-MA terpolymer | 0.17 |
| Substrate Core Layer | 100% EVA4 | 1.28 |
| Seal Layer | 100% LDPE | 0.26 |

Table V, below, provides another preferred multilayer film structure for use in the present invention, the film having a total thickness of 2 mils and a free shrink at 185° F. of 31 in the machine direction and 46 in the transverse direction.

TABLE V

| Layer Function | Layer Chemical Identity | Layer Thickness (mils) |
|---|---|---|
| Outside and abuse layer | 85% SSPE2 15% LLDPE3 | 0.18 |
| Core Layer | 100% LLDPE2 | 0.27 |
| Tie Layer | 100% EMA | 0.09 |
| $O_2$-Barrier layer | 96% VDC/MA #1; 2% epoxidized soybean oil; and 2% bu-A/MA/bu-MA terpolymer | 0.18 |
| Tie Layer & Indicator Layer | 100% EVA1 | 0.09 |
| Substrate Core Layer | 80% LLDPE2 20% LLDPE3 | 0.73 |
| Seal Layer | 90% SSPE1 10% MB1 | 0.45 |

Table VI, below, provides another preferred multilayer film structure for use in the present invention, the film having a total thickness of 2.2 mils and a free shrink at 185° F. of 36 in the machine direction and 51 in the transverse direction.

TABLE VI

| Layer Function | Layer Chemical Identity | Layer Thickness (mils) |
|---|---|---|
| Outside and abuse layer | 100% SSPE2 | 0.19 |
| Core Layer | 100% SSCPE3 | 0.29 |
| Tie Layer | 100% EVA2 | 0.10 |
| O2-Barrier layer | 96% VDC/MA #1; 2% epoxidized soybean oil; and 2% bu-A/MA/bu-MA terpolymer | 0.19 |
| Tie Layer & Indicator Layer | 100% EVA1 | 0.10 |
| Substrate Core Layer | 90% SSCPE3 10% EPD | 0.86 |
| Seal Layer | 100% SSPE1 | 0.48 |

In Tables II through VI, SSPE1 was Dow Affinity® PL 1280 ethylene/octene copolymer, having a density of 0.900 g/cc and a melt index of 6 g/10 min. SSPE2 was Dow Affinity® PL 1850, having a density of 0.902 g/cc and a melt index of 3 g/10 min. SSCPE3 was DPF 1150.01 single site catalyzed ethylene/octene copolymer having a density of 0.901 g/cc and a melt index of 0.9 g/10 min, obtained from Dow. LLDPE1 was Exxon Escorene® LL3003.32 linear low density polyethylene having a density of 0.9175 g/cc and a melt index of 3.2 g/10 min. LLDPE2 was Dow Attane® 4203, having a density of 0.905 g/cc and a melt index of 0.8 g/10 min. LLDPE3 is Dow Dowlex® 2045.03 linear low density polyethylene, having a density of 0.92 g/cc and a melt index of 1.1 g/10 min. LLDPE4 was Exceed® 4518PA ethylene/hexene copolymer having a density of 0.918 and a melt index of 4.5 g/10 min. LDPE was Ruxelle® V3401 ethylene/octene copolymer having a density of 0.911 g/cc and a melt index of 5.7 to 7.5 g/10 min, obtained from Huntsman. EVA1 was LD-713.93 ethylene/vinyl acetate copolymer, having a vinyl acetate content of 15 percent, a density of 0.933 g/cc and a melt index of 3.5 g/10 min, and was obtained from Exxon. EVA2 was Escorene® LD 761.36 ethylene/vinyl acetate copolymer having a density of 0.95 g/cc, a melt index of 5.7 g/10 min, and a vinyl acetate content of 28 percent, obtained from ExxonMobil. EVA3 was Escorene® LD 318.92 ethylene/vinyl acetate copolymer having a density of 0.93 g/cc, a melt index of 2 g/10 min, and a vinyl acetate content of 9 percent, obtained from ExxonMobil. EVA4 was Elvax® 3128 ethylene/vinyl acetate copolymer having a density of 0.928 g/cc, a melt index of 2 g/10 min, and a vinyl acetate content of 8.9%, obtained from DuPont. EMA was EMAC SP 1305 ethylene/methyl acrylate copolymer, having a methyl acrylate content of 20 percent, a density of 0.944 g/cc and a melt index of 2 g/10 min, also obtained from Exxon. EPD was Vistalon® 7800 ethylene/propylene/diene terpolymer, having a density of 0.87 g/cc and a melt index of 1.5 g/10 min, obtained from Exxon. VDC/MA was SARAN® MA-134 vinylidene chloride/methyl acrylate copolymer, obtained from the Dow Chemical Company. The epoxidized soybean oil was PLAS-CHEK® 775 epoxidized soybean oil, obtained from the Bedford Chemical Division of Ferro Corporation, of Walton Hills, Ohio. Bu-A/MA/bu-MA terpolymer was METABLEN® L-1000 butyl acrylate/methyl methacrylate/butyl methacrylate terpolymer, obtained from Elf Atochem North America, Inc., of 2000 Market Street, Philadelphia, Pa. 19103. MB1 was FSU 93E polyethylene masterbatch with slip and antiblock, having a density of 0.975 g/cc and a melt index of 7.5 g/10 min, obtained from A. Schulman. MB2 was 180637 light cream masterbatch having a density of 1.25 g/cc, obtained from Ampacet.

In the films of Tables I-VI, described above, the layer specified as an "Indicator" Layer would be a preferred layer for blending the indicator with the polymer which makes up that particular layer. Of course, this is not the only layer which could be used as the indicator layer. Moreover, the indicator could be printed onto the film, either on the inside surface of the film or, for example, onto the irradiated substrate before extrusion coating, so that the print is trapped between layers of the multilayer film.

Another film useful in the process of the present invention is a multilayer film, e.g. FS™ film made by Cryovac, Inc. for the packaging of fluid or pumpable foods in pouches made on vertical form/fill/seal apparatus. A film of this type has the general structure:

sealant/tie/nylon/EVOH/nylon/tie/sealant where the sealant comprise any of those disclosed herein; the tie layers are anhydride-modified polymeric olefinic or amidic adhesives; the nylon layers comprise any polyamide or copolyamide; and the EVOH (ethylene/vinyl alcohol copolymer) layer functions as the oxygen barrier layer. An oxygen scavenger can be suitably included as a layer within the above film structure, and an oxygen indicator could be in any one or more layers inside of the EVOH layer, or printed inside of the barrier layer or between any of the aforementioned layers inside the EVOH layer, or on the sealant layer of the film.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

What is claimed is:

1. A process for detecting a leak in a package, the process comprising:
   (A) preparing a package comprising a tray having an $O_2$-barrier film adhered to an inside surface thereof, and an $O_2$-sensitive product disposed on the tray, and a multilayer film over the product, the multilayer film also being sealed to the $O_2$-barrier film of the tray, the package having a low $O_2$ environment therein, the multilayer film comprising:
      (i) a leak-indicator layer in which an $O_2$-sensitive indicator is present throughout the leak-indicator layer; and
      (ii) an $O_2$-barrier layer outward of the leak-indicator layer;
   (B) illuminating the leak-indicator layer with a light containing a wavelength absorbed by the $O_2$-sensitive indicator, so that the $O_2$-sensitive indicator produces an emission of radiation in an amount inversely proportional to a concentration of $O_2$ present with the $O_2$-sensitive indicator; and
   (C) scanning the multilayer film manually or with an automated imaging system, while the $O_2$-sensitive indicator is emitting radiation, the scanning being carried out by comparing the amount of radiation emitted from at least two different regions of the multilayer film, where a difference in emitted radiation indicates the location of a leak.

2. The process according to claim 1, wherein the low $O_2$-environment is provided by carrying out at least one member selected from the group consisting of:
   (i) scavenging the $O_2$ inside the package by providing the package with an $O_2$-scavenger;
   (ii) evacuating atmosphere from within the package; and
   (iii) displacing atmospheric $O_2$ from the package.

3. The process according to claim 1, wherein results from the sensing and comparing of the radiation emitted from the at least two different scanned regions correlate with an absence of a leak into the package.

4. The process according to claim 1, wherein the $O_2$-sensitive product in the package having the at least one leak is removed from the package and repackaged in a new package.

5. The process according to claim 1, wherein the leak comprises at least one hole in the multilayer film.

6. The process according to claim 1, wherein the leak comprises at least one discontinuity in a seal of the film to itself or another component of the package.

7. The process according to claim 6, wherein the seal is a heat seal.

8. The process according to claim 1, wherein the $O_2$-sensitive product is a non-food product.

9. The process according to claim 1, wherein the package comprises a formed bottom member and a lidstock sealed to the formed bottom member, with the lidstock comprising the multilayer film.

10. The process according to claim 9, wherein the package comprises a modified atmosphere.

11. The process according to claim 1, wherein the $O_2$-sensitive indicator has been printed onto the film.

12. The process according to claim 1, wherein the $O_2$-sensitive product scavenges $O_2$ inside the package.

13. The process according to claim 12, wherein the $O_2$-sensitive product comprises food.

14. The process according to claim 1, wherein the package comprises a tray having a flange, with the multilayer film being over the product and adhered to the flange.

15. The process according to claim 1, wherein the $O_2$-barrier layer has an oxygen transmission rate of no more than 100 cc/m$^2$/24hr at 25° C., 0% RH, 1 atm (ASTM D 3985), the $O_2$-barrier layer comprising at least one member selected from the group consisting of polyester, polyamide, ethylene vinyl alcohol copolymer, polyvinyl alcohol homopolymer, polyvinyl chloride, homopolymer and copolymer of polyvinylidene chloride, polyethylene naphthalate, polyacrylonitrile homopolymer and copolymer, liquid crystal polymer, $SiO_x$, carbon, metal, and metal oxide.

16. The process according to claim 1, wherein the $O_2$-sensitive indicator comprises at least one member selected from the group consisting of metallo derivatives of octaethylporphyrin, tetraphenylporphyrin, tetrabenzoporphyrin, or the chlorins, bacteriochlorins, or isobacteriochlorins thereof.

17. The process according to claim 1, wherein the $O_2$-sensitive indicator comprises porphyrin.

18. The process according to claim 1, wherein atmosphere is evacuated between the food product and the film.

19. The process according to claim 1, wherein atmosphere is present between the food product and the multilayer film, the atmosphere containing $O_2$ in an amount of less than 5 weight percent.

20. The process according to claim 1, wherein the film further comprises an $O_2$-scavenger which comprises at least one member selected from the group consisting of:
  i) oxidizable organic compound and a transition metal catalyst,
  ii) ethylenically unsaturated hydrocarbon and a transition metal catalyst,
  iii) a reduced form of a quinone, a photoreducible dye, or a carbonyl compound which has absorbence in the UV spectrum,
  iv) a polymer having a polymeric backbone, cyclic olefinic pendent group, and linking group linking the olefinic pendent group to the polymeric backbone,
  v) a copolymer of ethylene and a strained, cyclic alkylene, and
  vi) ethylene/vinyl aralkyl copolymer,
  vii) ascorbate,
  viii) isoascorbate,
  ix) sulfite,
  x) ascorbate and a transition metal catalyst, the catalyst comprising a simple metal or salt, or a compound, complex or chelate of the transition metal,
  xi) a transition metal complex or chelate of a polycarboxylic acid, salicylic acid, or polyamine,
  xii) a tannin, and
  xiii) reduced metal.

21. The process according to claim 20, wherein the oxygen indicator and the oxygen scavenger are present in the form of a blend.

22. The process according to claim 21, wherein the blend is present in a layer of the film.

23. The process according to claim 1, wherein the oxygen indicator is encapsulated by an adhesive.

24. A process for detecting a leak in a package, the process comprising:
  (A) preparing a package comprising an $O_2$-sensitive product surrounded by a multilayer $O_2$-barrier film, the package having a low $O_2$ environment inside, the multilayer $O_2$-barrier film comprising:
    (i) a leak-indicator layer in which a an $O_2$-sensitive indicator is present throughout the leak-indicator layer; and
    (ii) an $O_2$-barrier layer outward of the leak-indicator layer;
  (B) illuminating the leak-indicator layer with a light containing a wavelength absorbed by the $O_2$-sensitive indicator, so that the $O_2$-sensitive indicator produces an emission of radiation in an amount inversely proportional to a concentration of $O_2$ present with the $O_2$-sensitive indicator; and
  (C) scanning the multilayer film manually or with an automated imaging system, while the $O_2$-sensitive indicator is emitting radiation, the scanning being carried out by comparing the amount of radiation emitted from at least two different regions of the multilayer film, where a difference in emitted radiation indicates the location of a leak.

25. The process according to claim 24, wherein the multilayer $O_2$-barrier film is sealed to itself to form a bag or pouch, and the package is prepared by placing the $O_2$-sensitive product into the bag or pouch, followed by evacuating the atmosphere from the bag or pouch and sealing across a top of the bag or pouch.

26. The process according to claim 25, wherein the multilayer film has a free shrink at 185° F. of at least 5 percent in both a machine direction and a transverse direction, and the process further comprises shrinking the multilayer film around the product after both the evacuating the bag our pouch and sealing across the top of the bag or pouch.

27. The process according to claim 24, wherein the $O_2$-sensitive indicator comprises at least one member selected from the group consisting of metallo derivatives of octaethylporphyrin, tetraphenylporphyrin, tetrabenzoporphyrin, or the chlorins, bacteriochiorins, or isobacteriochlorins thereof.

28. The process according to claim 24, wherein the wherein the $O_2$-sensitive indicator has been printed onto the film.

29. The process according to claim 1, wherein the film further comprises an $O_2$-scavenger which comprises at least one member selected from the group consisting of:
  i) oxidizable organic compound and a transition metal catalyst,
  ii) ethylenically unsaturated hydrocarbon and a transition metal catalyst,
  iii) a reduced form of a quinone, a photoreducible dye, or a carbonyl compound which has absorbence in the UV spectrum,
  iv) a polymer having a polymeric backbone, cyclic olefinic pendent group, and linking group linking the olefinic pendent group to the polymeric backbone,
  v) a copolymer of ethylene and a strained, cyclic alkylene,
  vi) ethylene/vinyl aralkyl copolymer,
  vii) ascorbate,
  viii) isoascorbate,
  ix) sulfite,
  x) ascorbate and a transition metal catalyst, the catalyst comprising a simple metal or salt, or a compound, complex or chelate of the transition metal,
  xi) transition metal complex or chelate of a polycarboxylic acid, salicylic acid, or polyamine,
  xii) tannin, and
  xiii) reduced metal.

* * * * *